United States Patent [19]

Barth et al.

[11] Patent Number: 5,304,237
[45] Date of Patent: Apr. 19, 1994

[54] CHROMIUM-FREE WOOD PRESERVATIVES

[75] Inventors: Volker Barth, Ludwigshafen; Helmut Hartner, Weinheim, both of Fed. Rep. of Germany

[73] Assignee: Rutgerswerke Aktiengesellschaft AG, Fed. Rep. of Germany

[21] Appl. No.: 6,454

[22] Filed: Jan. 21, 1993

[30] Foreign Application Priority Data

Feb. 19, 1992 [DE] Fed. Rep. of Germany ....... 4204940

[51] Int. Cl.$^5$ .................. C09D 5/14; A01N 55/02; B27K 3/52
[52] U.S. Cl. ............. 106/18.3; 106/18.32; 424/405; 514/64; 514/500; 514/642; 514/947; 556/112
[58] Field of Search ............... 106/18.3, 18.32; 514/500, 64, 642, 947; 424/405; 556/112

[56] References Cited

U.S. PATENT DOCUMENTS

| | | | |
|---|---|---|---|
| 2,924,505 | 2/1960 | Page, Jr. ................. | 106/18.3 |
| 4,496,613 | 1/1985 | Zagefka et al. ........... | 106/18.32 |
| 4,613,373 | 9/1986 | Umeno et al. ............ | 106/18.3 |
| 4,661,157 | 4/1987 | Beauford et al. ......... | 106/18.3 |
| 4,808,407 | 2/1989 | Hein et al. .............. | 106/18.32 |
| 4,970,201 | 11/1990 | Giebeler et al. ......... | 514/64 |
| 5,078,912 | 1/1992 | Goettsche et al. ........ | 252/400.53 |

FOREIGN PATENT DOCUMENTS 3447027  5/1987  Fed. Rep. of Germany .

*Primary Examiner*—Anthony Green
*Attorney, Agent, or Firm*—Bierman and Muserlian

[57] ABSTRACT

A water-soluble chromium-free wood preservative comprising at least one copper salt and an alkanolamine and a polymeric quaternary ammonium borate formed by simultaneous reaction of (A) an amine selected from the group consisting of

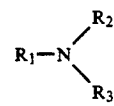

I

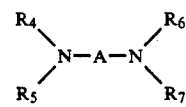

II wherein $R_1$ is alkyl or alkenyl of 8 to 22 carbon atoms or when $R_2$ and $R_3$ are $-(C_2H_4O)_x-H$ or $-(C_3H_6O)_x-H$, $R_1$ is alkyl of 1 to 22 carbon atoms, $R_2$ is selected from the group consisting of hydrogen, alkyl of 1 to 22 carbon atoms, $-(C_2H_4O)_x-H$, $-(C_3H_6O)_x-H$ and $-CH_2-CH_2-NH_2$, $R_3$ is selected from the group consisting of hydrogen, $-(C_2H_4O)_x-H$, $-(C_3H_6O)_x-H$ and $CH_2-CH_2-CH_2NH_2$, $R_4$ and $R_6$ are individually alkyl of 1 to 4 carbon atoms or $-(CH_2H_4O)_x-H$ or $-(C_3H_6O)_x-H$, $R_5$ and $R_2$ are individually $-(C_2H_4O)_x-H$ or $-(_3H_6O)_x-H$, A is selected from the group consisting of $-(CH_2)_n-$, $-(CH_2-CH_2OCH_2)_n-$ and $-(CH_2CH_2NHCH_2CH_2)_n-$, x is an integer of 1 to 55 and n is an integer of 1 to 20, (B) 2 to 20 moles of ethylene oxide or propylene oxide and (C) 0.6 to 1.5 moles of a member of the group consisting of boric acid, boric acid salts and boric acid esters per mole of nitrogen equivalent of (A) useful for impregnating wood exposed to weather conditions or installed in contact with soil.

10 Claims, No Drawings

CHROMIUM-FREE WOOD PRESERVATIVES

STATE OF THE ART

Chromate containing compositions have been used for wood preservatives but for toxicological and environmental reasons, it is desirable to develop chromate-free preservatives. DE-C 3,447,027 describes wood preservatives containing copper, 0.5 to 2.5 g-atoms of boron and 2 to 10 moles of an alkanolamine per g-atom of copper while DE-A-3,520,394 describes a wood preservative in the form of a copper salt solution adjusted to a pH of at least 8 with an alkanolamine and optionally an alkali metal salt. Such agents may also contain a borate or other water-soluble fungicides, particularly up to 25% by weight of the final product of quaternary ammonium salts.

Gradual evaporation of the alkanolamine from wood impregnated with such toxicologically-safe agents or neutralization by wood ingredients fixes the copper salts. Even with the additional use of quaternary ammonium salts, the preservative effect, preferably long term, is insufficient. The addition of other fungicides also offers no substantial improvement.

A particular problem is the ubiquitous copper-resistant fungi of the Porea genus which cause the copper in a copper-alkanolamine system to return to a water-soluble form which is then washed out.

OBJECTS OF THE INVENTION

It is an object of the invention to provide a salt-like water-soluble agent suitable for the protection of wood highly vulnerable to fungus action, which is chromium-free, toxicologically just as safe as the known copper-alkanolamine-based agents, but which shows a much improved action, particularly long-term action, and is not impaired by the copper-resistant fungi.

It is another object of the invention to provide a novel wood preservation method.

These and other objects and advantages of the invention will become obvious from the following detailed description.

THE INVENTION

The novel compositions of the invention are water-soluble chromium-free wood preservatives comprising at least one copper salt and an alkanolamine and a polymeric quaternary ammonium borate formed by simultaneous reaction of (A) an amine selected from the group consisting of $$R_1-N\begin{array}{c}R_2\\\\R_3\end{array} \quad \text{I}$$

$$\begin{array}{c}R_4\\\\R_5\end{array}N-A-N\begin{array}{c}R_6\\\\R_7\end{array} \quad \text{II}$$

wherein $R_1$ is alkyl or alkenyl of 8 to 22 carbon atoms or when $R_2$ and $R_3$ are $-(C_2H_4O)_x-H$ or $-(C_3H_6O)_x-H$, $R_1$ is alkyl of 1 to 22 carbon atoms, $R_2$ is selected from the group consisting of hydrogen, alkyl of 1 to 22 carbon atoms, $-(C_2H_4O)_x-H$, $-(C_3H_6O)_x-H$ and $-CH_2-CH_2-NH_2$, $R_3$ is selected from the group consisting of hydrogen, $-(C_2H_4O)_x-H$, $-(C_3H_6O)_x-H$ and $CH_2-CH_2-CH_2NH_2$, $R_4$ and $R_6$ are individually alkyl of 1 to 4 carbon atoms or $-(C_2H_4O)_x-H$ or $-(C_3H_6O)_x-H$, $R_5$ and $R_2$ are individually $-(C_2H_4O)_x-H$ or $-(_3H_6O)_x-H$, A is selected from the group consisting of $-(CH_2)_n-$, $-(CH_2-CH_2OCH_2)_n-$ and $-(CH_2CH_2NHCH_2CH_2)_n-$, x is an integer of 1 to 55 and n is an integer of 1 to 20 (B) 2 t 20 moles of ethylene oxide or propylene oxide and (C) 0.6 to 1.5 moles of a member of the group consisting of boric acid, boric acid salts and boric acid esters per mole of nitrogen equivalent of (A).

It has been found that by adding polymeric quaternary ammonium borate to wood preservatives containing copper salt and alkanolamine, the introduced amount of the resulting agents can be reduced drastically. Thus, for example, by addition of 6.5% by weight of polymeric quaternary ammonium borate to a copperalkanolamine-based agent, the limit values against wood-destroying basidiomycetes are reduced by a factor of 10.

Even in view of the fact that it is known from EP-A-0,355,316 that polymeric quaternary ammonium borates are suitable as wood preservatives, this result must be regarded as a surprising synergistic effect of the active substances used. In particular, it is unexpected that this combination of active substances of the invention is effective also against the copper-resistant fungi, at the same time exceeding the insecticidal effect of the formulations which contain polymeric quaternary ammonium borates, further increasing it, and that it prevents a degradation of the fixed copper salts and thus makes possible long-term protection of the wood.

The agents of the invention preferably contain 5 to 50% by weight of copper salt, 5 to 50% by weight of alkanolamine, 2 to 50% by weight of polymeric quaternary ammonium borate and optionally up to 5% by weight of alkali metal and up to 50% by weight of other inorganic or organic fungicidal and/or insecticidal substances or mixtures, particularly boric acid or one or more water-soluble borates and also optionally small amounts of adjuvant and water, in each instance totaling 100% by weight.

These agents are produced preferably as concentrates, which before use are diluted with water to a concentration of 1 to 20% (of the sum of all above named active substances). These diluted aqueous agents can be used for the treatment of wood by all customary methods such as brushing, spraying, immersion or pressure impregnation.

Examples of suitable water-soluble copper salts are all commercial copper salts such as copper sulfate, fluoroborate, hydroxide, borate, fluoride, carbonate, oxychloride, formate or acetate. The preferred copper salt is basic copper carbonate with the simplified formula $CU(OH)_2-CuCO_3$.

Examples of alkanolamine are isopropanolamine, 1,2-diaminoethanol, diethanolamine, dimethylethanolamine and triethanolamine. The preferred alkanolamine is ethanolamine. The quantity of alkanolamines to be added should preferably be such that it is sufficient for complexing the copper (1 g-atom copper requires 4 molar equivalents of amine) and that if applicable, alkanolamine salts of any additionally used fungicidal anions (fluoride, borate, fluoroborate and fluorophosphate) or acid esters can form.

The polymeric quaternary ammonium borates are obtained by simultaneous reaction of amines of the formulae

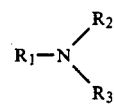

I or

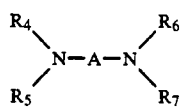

II with 2 to 20, preferably 3 to 10, moles of ethylene oxide or propylene oxide and 0.6 to 1.5, preferably 1 mole of boric acid, boric acid ester, or salts of boric acid per mole of nitrogen equivalent in each instance, where $R_1$ is alkyl or alkenyl of 8 to 22 carbon atoms or, when $R_2$ and $R_3$ are $-(C_2H_4O)_xH$ or $-(C_3H_6O)_xH$, $R_1$ can also be alkyl of 1 to 4 carbon atoms, $R_2$ is hydrogen, alkyl of 1 to 22 carbon atoms, $-(C_2H_4O)_xH$, $-(C_3H_6O)_xH$ or $CH_2CH_2CH_2NH_2$, $R_4$ and $R_6$ are alkyl of 1 to 4 carbon atoms or $-(C_2H_4O)_xH$, $-(C_3H_6O)_xH$, $R_5$ and $R_7$ are $-(CH_2)_n-$, $-(CH_2CH_2OCH_2OH)_n-$ or $-(CH_2CH_2NHCH_2CH_2)_n$, x is an integer from 1 to 55, and n is an integer from 1 to 20.

Preferred as amines of the above formulae are 1) amines of Formula I wherein $R_1$ is alkyl of 8 to 22 carbon atoms, $R_2$ is alkyl of 8 to 22 carbon atoms or alkyl of 1 to 4 carbon atoms, and $R_3$ is hydrogen or $-(C_2H_4O)_xH$ or $-(C_3H_6O)_xH$. 2) amines of Formula I where $R_1$ is alkyl of 8 to 22 carbon atoms, and $R_2$ and $R_3$ are hydrogen. 3) amines of Formula I where $R_1$ is alkyl of 1 to 4 carbon atoms or alkyl of 8 to 22 carbon atoms, and $R_2$ and $R_3$ are $-(C_2H_4O)_xH$ or $-(C_3H_6O)_xH$, the sum of the ethylene oxide groups in both $R_2$ and $R_3$ being 2 to 20. 4) amines of Formula I where $R_1$ is alkyl of 8 to 22 carbon atoms, $R_2$ is hydrogen or $-CH_2CH_2CH_2NH_2$, and $R_3$ is $-CH_2CH_2CH_2NH_2$. 5) amines of Formula II where A, $R_4$, $R_5$, $R_6$ and $R_7$ have the meanings stated above and where the sum of all ethylene oxide groups is 4 to 30.

For the alkylene oxide groups of the formulas $-(C_2H_4O)_xH$ and $-(C_3H_6O)_xH$, the group $-(C_2H_4O)_xH$ is preferred. Instead of pure polyoxethylene and polyoxpropylene groups, groups of both ethylene oxide and propylene oxide units may be present.

The reaction of the amines with the boric acid and the alkylene oxide takes place in that the respective amine and the boric acid are placed in an autoclave with the alkylene oxide being proportioned in. The reaction temperature is generally 60° to 130° C., preferably 60° to 125° C., more particularly 60° to 100° C. The reaction pressure is 50 to 600 kPa. The addition of the alkylene oxide under these reaction conditions occurs over a period of 1 to 5 hours. For final reaction, the mixture is kept at the stated pressure for 3 to 12 hours at a temperature of 70° to 120° C., preferably 70° to 100° C.

Instead of boric acid, esters thereof such as trimethyl boric acid ester or salts thereof such as Na borate can be used. Water and polyglycols are formed as by-products in the reaction.

The polymeric quaternary ammonium compounds obtained contain essentially as structure characteristic groups of the formula

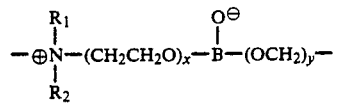

or respectively groups of the formula

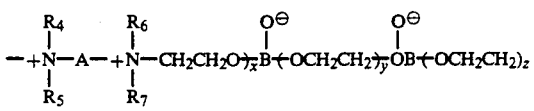

when the reaction was made with ethylene oxide. They must be regarded as polymeric betaines.

In the following examples, there are described several preferred embodiments to illustrate the invention. However, it is to be understood that the invention is not intended to be limited to the specific embodiments.

EXAMPLE 1

In a one-liter glass autoclave, 194.4 g (0.80 mole) of a mixture of 9.6% (n/n) octylamine, 89% (n/n) of dioctylamine and 1.4% (n/n) of trioctylamine (amine index 230.9) and 49.4 g (0.80 mole) of anhydrous boric acid were charged and the mixture was heated to 80° C. with stirring. To the then liquid reaction mixture, 158 ml (3.20 moles) of liquid ethylene oxide were added at an internal temperature of 80° to 100° C. within 2.5 hours so that the internal pressure did not exceed 460 kPa. Then the mixture was allowed to react for another 6 hours and after this period, the pressure had dropped to 40 kPa.

The reaction product, liquid and homogeneous at 25° C. was characterized by the following analytical values: Viscosity (Haake RV 12, 25° C., 25° C., D=21 s$^{-1}$): 39 Pa, water (k. Fischer): 10% (m/m), ethylene glycol: 7.4% (m/m), diethylene glycol: 3.3% (m/m), triethylene glycol: 1.7% (m/m), pH value: 9.8. From an ethylene oxide balance, a statistical value of 3 moles of bound ethylene oxide per nitrogen equivalent was calculated and the product was adjusted with water to an active substance content of 65%.

EXAMPLE 2

Wood preservative concentrates of the following composition (in per cent by weight) were produced:

| | Products | | | | |
|---|---|---|---|---|---|
| | A | B | C | D | E |
| Active substances | | | | | |
| Ethanolamine | 38.55 | 38.55 | 38.55 | — | — |
| Basic copper carbonate | 20.53 | 20.53 | 20.53 | — | — |
| Copper sulfate | | | | | 20.53 |
| Boric acid | 8.00 | 8.00 | 8.00 | — | 8.00 |
| N-alkybenzyl-dimethyl ammonium chloride | — | — | 10.00 | — | — |
| Polymeric quaternary ammonium borate (per Ex. 1) | 10.00 | — | — | 100 | 10.00 |
| Water | 22.92 | 32.92 | 22.92 | — | 62.47 |

The concentrates were adjusted with water to a 3% concentration of the active substances. With these agents, dry pinewood samples are impregnated. The limit values against wood-destroying basidiomycetes were determined after elutriation (per DIN EN 113 and DIN EN 84).

| Agents | | | | |
|---|---|---|---|---|
| A | B | C | D | E |
| 4.5 | 45.0 | 39.0 | 9.5 | >30.0 |

After 12 months of storage in moist soil, almost no fungicidal copper was left in samples B, C and E, while sample A was almost unchanged.

EXAMPLE 3

Specimens of pine sapwood were impregnated according to EN 117 with solutions of composition A from Example 2, which had been adjusted by addition of water to active substance concentrations of 5, 3.5 and 2 mass %, and then dried. The sample woods were then tested according to E 117 after EN 84 for their effectiveness against the termites Reticulitermes santonensis (250 workers, 1 soldier, 1 nymph per batch).

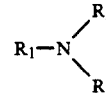

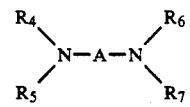

wherein $R_1$ is alkyl or alkenyl of 8 to 22 carbon atoms or when $R_2$ and $R_3$ are $-(C_2H_4O)_x-H$ or $-(C_3H_6O)_x-H$, $R_1$ is alkyl of 1 to 22 carbon atoms, $R_2$ is selected from the group consisting of hydrogen, alkyl of 1 to 22 carbon atoms, $-(C_2H_4O)_x-H$, $-(C_3H_6O)_x-H$ and $-CH_2-CH_2-NH_2$, $R_3$ is selected from the group consisting of hydrogen, $-(C_2H_4O)_x-H$, $-(C_3H_6O)_x-H$ and $CH_2-CH_2-CH_2NH_2$, $R_4$ and $R_6$ are individually alkyl of 1 to 4 carbon atoms or $-(C_2H_4O)_x-H$ or $-(C_3H_6O)_x-H$, $R_5$ and $R_2$ are individually $-(C_2H_4O)_x-H$ or $-(_3H_6O)_x-H$, A is selected from the group consisting of $-(CH_2)_n-$, $-(CH_2-CH_2OCH_2)_n-$ and $-(CH_2CH_2NHCH_2CH_2)_n-$, x is an integer of 1 to 55 and n is an integer of 1 to 20, (B) 2 to

| Samples Type | No. | Tested concentration Mass % | Solution absorption per sample in g | Preservative absorption in kg/m³ per sample | mean | Surviving animals after 8 weeks Workers % rounded | Soldiers (S) Nymphs (N) | Evaluation* |
|---|---|---|---|---|---|---|---|---|
| Untreated controls | 1 | | 0 | 0 | | 79 | S/N | 4 |
| | 2 | 0 | 0 | 0 | 0 | 73 | S/N | 4 |
| | 3 | | 0 | 0 | | 71 | S/N | 4 |
| Controls treated with solvents or diluents | 4 | | 13.5 | 0 | | 76 | S/N | 4 |
| | 5 | 0 | 13.5 | 0 | 0 | 61 | S/N | 4 |
| | 6 | | 13.5 | 0 | | 77 | S/N | 4 |
| Treated | 7 | | 13.6 | 14.5 | | 0 | 0 | 1 |
| | 8 | 2 | 13.5 | 14.4 | 14.3 | 0 | 0 | 1 |
| | 9 | | 13.3 | 14.1 | | 0 | 0 | 1 |
| | 10 | | 12.4 | 23.1 | | 0 | 0 | 1 |
| | 11 | 3.5 | 12.6 | 23.5 | 23.2 | 0 | 0 | 1 |
| | 12 | | 12.3 | 23.0 | | 0 | 0 | 1 |
| | 13 | | 13.6 | 36.3 | | 0 | 0 | 1 |
| | 14 | 5 | 12.8 | 34.1 | 34.5 | 0 | 0 | 1 |
| | 15 | | 12.4 | 33.0 | | 0 | 0 | 1 |

*Evaluation scores:
0 = no attack
1 = traces of gnawing
2 = light attack
3 = medium attack
4 = strong attack When impregnated with the preservative, the treated samples showed slight traces of gnawing at a test concentration of 2% (mean absorption quantity 14.3 kg/m³), 3.5% (mean absorption quantity 23.2 kg/m³) and 5% (mean absorption quantity 34.5 kg/m³) but the animals did not survive.

Various modifications of the compositions and method of the invention may be made without departing from the spirit or scope thereof and it is to be understood that the invention is intended to be limited only as defined in the appended claims.

What we claim is:

1. A water-soluble chromium-free wood preservative comprising at least one copper salt and an alkanolamine and a polymeric quaternary ammonium borate formed by simultaneous reaction of (A) an amine selected from the group consisting of 20 moles of ethylene oxide or propylene oxide and (C) 0.6 to 1.5 moles of a member of the group consisting of boric acid, boric acid salts and boric acid esters per mole of nitrogen equivalent of (A).

2. The preservative of claim 1 wherein 3 to 10 moles of (B) are used.

3. The preservative of claim 1 wherein about 1 mole of (C) is used.

4. The preservative of claim 1 in concentrate form which is diluted before use to 1 to 20% by weight.

5. The concentrate of claim 4 containing 5 to 50% by weight of the polymeric quaternary ammonium borate.

6. The preservative of claim 1 wherein (C) is boric acid or a water-soluble salt of boric acid.

7. The preservative of claim 1 also containing a pesticidally effective amount of at least one fungicide or insecticide or mixtures thereof.

8. A method of preserving wood comprising impregnating wood with a preservative effective amount of a preservative of claim 1.

9. The method of claim 8 wherein the preservative also contains a pesticidally effective amount of a fungicide and/or an insecticide.

10. The method of claim 8 wherein the preservative is a concentrate which is diluted with water before use to a weight concentration of 1 to 20%.

* * * * *